US008989853B2

(12) United States Patent
Zong (10) Patent No.: US 8,989,853 B2
(45) Date of Patent: Mar. 24, 2015

(54) ECG MONITORING WITH REDUCED FALSE ASYSTOLE ALARMS (75) Inventor: Wei Zong, Belmont, MA (US)

(73) Assignee: Koninklijke Philips N.V., Eindhoven (NL)

(*) Notice: Subject to any disclaimer, the term of this patent is extended or adjusted under 35 U.S.C. 154(b) by 175 days.

(21) Appl. No.: 13/321,841

(22) PCT Filed: May 12, 2010

(86) PCT No.: PCT/IB2010/052123
§ 371 (c)(1),
(2), (4) Date: Nov. 22, 2011

(87) PCT Pub. No.: WO2010/146481
PCT Pub. Date: Dec. 23, 2010

(65) Prior Publication Data
US 2012/0078131 A1 Mar. 29, 2012

Related U.S. Application Data (60) Provisional application No. 61/218,092, filed on Jun. 18, 2009.

(51) Int. Cl.
A61B 5/04 (2006.01)
A61B 5/0452 (2006.01)
(Continued)

(52) U.S. Cl.
CPC .............. A61B 5/0452 (2013.01); A61B 5/021 (2013.01); A61B 5/024 (2013.01); A61B 5/0468 (2013.01)
USPC .......................................................... 600/513

(58) Field of Classification Search
CPC .......................... A61B 5/0452; A61B 5/0205
USPC ............................ 600/513, 301, 528; 607/18
See application file for complete search history.

(56) References Cited

U.S. PATENT DOCUMENTS 6,304,773 B1 * 10/2001 Taylor et al. ................... 600/515
6,801,802 B2 * 10/2004 Sitzman et al. ................ 600/513
(Continued)

FOREIGN PATENT DOCUMENTS

JP 2000000218 A 1/2000
JP 2000312668 A 11/2000
(Continued)

OTHER PUBLICATIONS

Aboukhalil, A., et al.; Reducing false alarm rates for critical arrhythmias using the arterial blood pressure waveform; 2008; Journal of Biomedical Informatics; 41:442-451.
(Continued)

Primary Examiner — Christopher D Koharski
Assistant Examiner — Jeremiah Kimball (57) ABSTRACT A patient monitor comprises: an electrocardiograph (14, 20) monitoring an electrocardiographic signal (40) of a patient (10); a secondary physiological signal monitor (16, 20) monitoring a second physiological signal (50) of the patient concurrently with the electrocardiograph monitoring the electrocardiographic signal of the patient; an alarm condition detector (42, 44) configured to detect an alarm condition based on the electrocardiographic signal of the patient; an alarm condition validator (52, 54, 56) configured to validate the alarm condition based on pulse regularity of a pulsatile component of the concurrently monitored second physiological signal of the patient; and an alarm indicator (24, 26, 58) configured to generate a human perceptible alarm conditional upon both the alarm condition detector detecting an alarm condition and the alarm condition validator validating the alarm condition.

12 Claims, 5 Drawing Sheets (51) Int. Cl.
    *A61B 5/021*    (2006.01)
    *A61B 5/024*    (2006.01)
    *A61B 5/0468*   (2006.01)

(56) References Cited

U.S. PATENT DOCUMENTS

| | | | |
|---|---|---|---|
| 7,035,684 B2* | 4/2006 | Lee | 600/513 |
| 7,460,902 B2* | 12/2008 | Kaski | 600/513 |
| 7,680,532 B2 | 3/2010 | Wiesel | |
| 2003/0060723 A1* | 3/2003 | Joo et al. | 600/510 |
| 2004/0039420 A1* | 2/2004 | Jayne et al. | 607/5 |
| 2004/0111014 A1 | 6/2004 | Hickle | |
| 2008/0214904 A1* | 9/2008 | Saeed et al. | 600/301 |
| 2008/0269626 A1 | 10/2008 | Gallagher et al. | |
| 2008/0275349 A1 | 11/2008 | Halperin et al. | |
| 2009/0030334 A1* | 1/2009 | Anderson et al. | 600/528 |
| 2010/0114222 A1* | 5/2010 | Gunderson et al. | 607/8 |

FOREIGN PATENT DOCUMENTS

| | | |
|---|---|---|
| JP | 2001198094 A | 7/2001 |
| WO | 2008075288 A2 | 6/2008 |

OTHER PUBLICATIONS

Sun, J.X., et al.; A Signal Abnormality Index for Arterial Blood Pressure Waveforms; 2006; Computers in Cardiology; vol. 33:13-16.

Zong, W., et al.; Reduction of false arterial blood pressure alarms using signal quality assessment and relationships between the electrocardiogram and arterial blood pressure; 2004; Medical & Biological Engineering & Computing; 42(5)698-706.

* cited by examiner

ECG MONITORING WITH REDUCED FALSE ASYSTOLE ALARMS

CROSS REFERENCE TO RELATED APPLICATIONS

This application claims the benefit of U.S. provisional application Ser. No. 61/218,092 filed Jun. 18, 2009, which is incorporated herein by reference.

The following relates to the medical arts, medical monitoring arts, physiological monitoring arts, patient safety arts, and related arts.

Electrocardiography (ECG) monitoring is well known as a conventional patient monitoring technique. A skilled cardiologist or other skilled medical diagnostician can infer substantial information from the waveform shape, repetition rate, and other aspects of the ECG signal waveform as a function of time. For more routine patient monitoring, the ECG provides continuous information regarding the heart rate, and a nurse or other medical attendant can identify an urgent patient problem based on large changes in the ECG signal.

Of particular interest for patient monitoring is fast and accurate detection of heart arrhythmias such as ventricular fibrillation or asystole. Ventricular fibrillation is a condition in which the heart loses regulation and begins to beat in a random or pseudorandom fashion—this condition requires immediate attention. Asystole is even more urgent—this is colloquially referred to as a "flatline" condition, in which the heart ceases beating altogether, a condition also known as cardiac arrest. Asystole leads to brain damage and death within minutes, and therefore must be treated immediately. In a hospital or other medical facility detection of asystole initiates a "code blue" event in which a crash team is called to attempt to resuscitate the patient.

ECG advantageously provides fast and generally accurate detection of asystole. It is difficult for ECG to fail to detect asystole, because the ECG monitors the heart rate itself—if the ECG apparatus fails, the result is likely to be a null signal similar to a "flatline" condition, which will result in a code blue event. As a result, ECG is highly unlikely to give a "false negative", that is, to fail to detect a real asystole event.

However, ECG can be susceptible to generating "false positive" events, that is to indicate asystole when in fact the patient's heart is beating normally (or at least is not in asystole). Such false positive events can be triggered by the detachment or other failure of one or more ECG electrodes, caused for example by routine patient movement. Other causes of false positive events include ECG "glitches", signal saturation, or so forth. Each false positive asystole detection results in medical personnel reacting in an emergency mode, and can trigger an unnecessary code blue event.

It has been estimated that about 90% or more of all asystole detection events are actually false positive events, in which the patient is not undergoing cardiac arrest but the ECG falsely indicates a flatline condition. The costs of these false positive asystole detection events include lost time of medical professionals responding to the false event, stress on all medical professionals in the area, stress on the patient who finds his or her medical monitor suddenly emitting a loud audible alarm or otherwise indicating an emergency condition, and desensitization of medical personnel to the point where they may fail to respond in an appropriately urgent fashion to an actual patient cardiac arrest.

On the other hand, the cost of a single false negative asystole detection event is that the patient may suffer brain damage or death due to delay in providing medical assistance to the patient undergoing cardiac arrest.

Attempts have been made to reduce the number of false positive asystole detection events by analyzing the ECG signal, or by augmenting the ECG signal with other concurrently acquired patient monitoring information such as arterial blood pressure. For example, Aboukhalil et al., "Reducing false alarm rates for critical arrhythmias using arterial blood pressure waveform", Journal of Biomedical Informatics vol. 41, pp. 442-51 (2008) discloses an approach in which the ECG signal is augmented by arterial blood pressure (ABP) pulsing rate. In this approach, the asystole alarm is suppressed if the pulse-to-pulse interval for the ABP signal is shorter than a threshold value. This approach assumes the APB pulsing rate correlates with the cardiac cycle, so that if the ABP pulsing interval is shorter than the threshold value then the APB pulses correspond to cardiac cycling, indicating that the flatline ECG must be in error.

Problematically, existing techniques for reducing false positive asystole detection events also substantially increase the likelihood of generating a false negative event so as to "miss" a real asystole event. For example, the approach of Aboukhalil et al. could potentially suppress a real asystole detection alarm if noise or artifacts in the APB signal were to produce a sequence of APB pulses at intervals below the threshold value.

The following provides new and improved apparatuses and methods which overcome the above-referenced problems and others.

In accordance with one disclosed aspect, a patient monitor comprises: an electrocardiograph monitoring an electrocardiographic signal of a patient; a secondary physiological signal monitor monitoring a second physiological signal of the patient concurrently with the electrocardiograph monitoring the electrocardiographic signal of the patient; an alarm condition detector configured to detect an alarm condition based on the electrocardiographic signal of the patient; an alarm condition validator configured to validate the alarm condition based on pulse regularity of a pulsatile component of the concurrently monitored second physiological signal of the patient; and an alarm indicator configured to generate a human perceptible alarm conditional upon both the alarm condition detector detecting an alarm condition and the alarm condition validator validating the alarm condition In accordance with another disclosed aspect, a patient monitoring method comprises: monitoring an electrocardiographic signal of a patient; monitoring a second physiological signal of the patient concurrently with the monitoring of the electrocardiographic signal of the patient; detecting an alarm condition based on the electrocardiographic signal of the patient; validating the alarm condition based on pulse regularity of a pulsatile component of the concurrently monitored second physiological signal of the patient; and generating a human perceptible alarm conditional upon the alarm condition being validated by the validating.

In accordance with another disclosed aspect, a storage medium is disclosed which stores instructions executable by a digital processor to perform a patient monitoring method as set forth in the immediately preceding paragraph.

One advantage resides in providing a reduction in false positive asystole detection events without concurrent suppression of false negative asystole detection events.

Another advantage resides in providing a substantial reduction in false positive asystole events thus enhancing accuracy of ECG-based asystole event detection.

Further advantages will be apparent to those of ordinary skill in the art upon reading and understand the following detailed description.

It is disclosed herein to validate ECG asystole event alarms based on rhythm and amplitude information of a secondary physiological signal such as an arterial blood pressure signal or plethysmogram signal. The disclosed validation technique not only utilizes instant pulse-to-pulse interval of the secondary physiological signal, but also incorporates a short-term pulse regularity feature to verify ECG asystole events. A pulse regularity index (PRI) is disclosed, which summarizes, on a beat-by-beat basis, the short-term secondary physiological signal pulse rhythm and amplitude feature in terms of regularity. The PRI value represents the extent of short-term pulse regularity and is used to validate ECG asystole alarms.

Regular pulses (in terms of rhythm and amplitude) do not happen during asystole. Regular pulses are also unlikely to be generated by random noise or artefacts. Accordingly, the disclosed validation approach employing the PRI has high reliability in keeping true ECG asystole alarms while rejecting false ECG asystole alarms. The PRI is computed on a beat-by-beat basis at least during an ECG asystole alarm. The PRI value computed for the last pulse detection cycle (prior to the asystole event) is checked for validating the asystole alarm. This processing is therefore computationally efficient and provides fast validation of the ECG asystole alarm.

Figure 1:
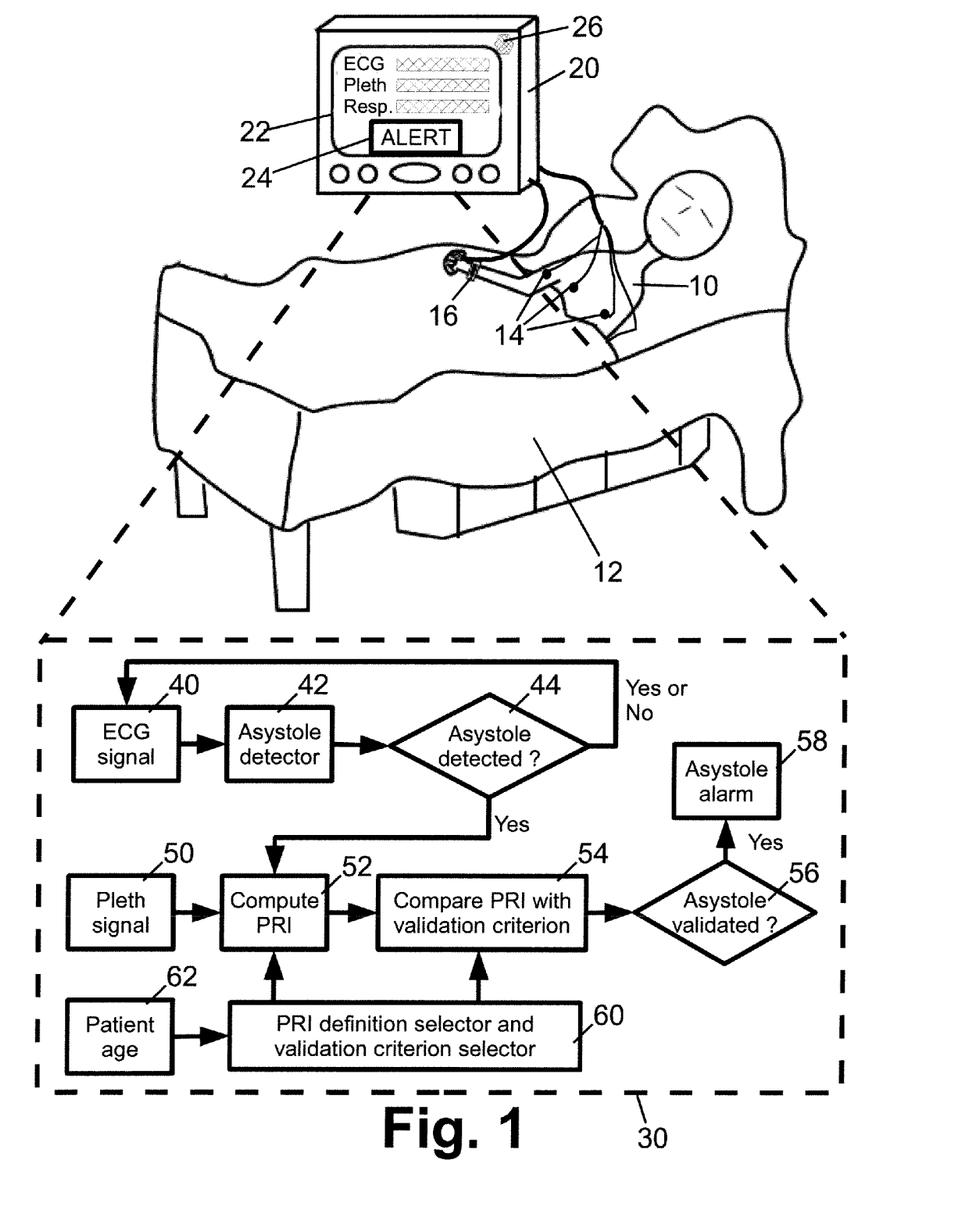
FIG. 1 diagrammatically shows a patient monitoring system with detection and validation of asystole events.

With reference to FIG. 1, a patient 10 is disposed on a bed 12 or, alternatively, may be standing, sitting, in an ambulance or other emergency response vehicle, or otherwise disposed. Although the illustrated patient 10 is a human patient, it is also contemplated for the patient to be an animal, such as in a veterinary setting. Electrodes 14 are attached to the patient 10 in order to acquire electrocardiographic (ECG) signals. A sensor 16 detects a secondary physiological signal. For example, the sensor 16 may be a pulse oxymeter mounted on a finger, toe, or other part of the patient 10, or other sensor detecting a plethysmogram (pleth) signal, or an arterial blood pressure (ABP) sensor, or other blood pressure sensor, or so forth. The sensor 16 detects a secondary physiological signal (that is, other than the ECG signal detected by the electrodes 14). The secondary physiological signal exhibits a pulsatile signal component with substantial regularity in pulse interval and pulse amplitude during the normal physiological condition.

A patient monitor 20 monitors the ECG signal detected by the ECG electrodes 14, and monitors the pleth signal, ABP signal, or other secondary physiological signal detected by the sensor 16. In other words, the patient monitor 20 serves as both an electrocardiograph that monitors the ECG signal and as a secondary physiological signal monitor that monitors the pleth signal, ABP signal, or other secondary physiological signal detected by the sensor 16. Alternatively, a separate electrocardiograph and secondary physiological signal monitor may be provided (not illustrated). The patient monitor 20 includes a display 22 that displays one or more monitored physiological parameters, such as the ECG signal, the plethysmogram (pleth) signal, and a respiration signal in the illustrative example of FIG. 1.

The patient monitor 20 further includes one or more alarm indicators for generating a human-perceptible alarm during an alarm condition, such as an illustrative visual alarm indicator 24 that is shown on the display 22 during an alarm condition (preferably in a distinctive and noticeable manner such as flashing, in red, or so forth), and an illustrative speaker 26 that generates an audible alarm during an alarm condition. Alarm conditions that may be visually and audibly indicated by the elements 24, 26 include at least an asystole event, and may optionally include other life- or health-threatening events such as a ventricular fibrillation event, a respiratory failure, or so forth. In addition to or alternative to the illustrative alarm indicators 24, 26, it is contemplated for an alarm condition to be indicated by a remote indicator located at a nurses' station (not shown). A single alarm indicator type (either visual or audible) is also contemplated.

A digital processor 30 is provided to process monitored physiological signals such as the monitored ECG signal and the monitored ABP, pleth, or other secondary physiological signal, in order to detect and validate an alarm condition. The digital processor 30 may be variously located and embodied, and may comprise two or more digital processors. In the illustrative embodiment, the digital processor 30 is a component of the patient monitor 20; alternatively or additionally, the digital processor may be disposed at a nurses' station and embodied as a computer that receives and processes physiological signals monitored by the patient monitor 20, or so forth. As another example, the digital processor may include a first processor disposed in the patient monitor 20 that acquires the ECG and second physiological signals and performs alarm detection, and a second digital processor disposed in a computer of the nurses' station which performs alarm validation.

It is also to be appreciated that the alarm detection and validation techniques disclosed herein can be suitably embodied as a storage medium storing instructions executable by the digital processor 30 to perform the disclosed alarm detection and validation techniques. Such a storage medium may, for example, comprise one or more of the following: a hard disk or other magnetic storage medium; an optical disk or other optical storage medium; a random access memory (RAM), read-only memory (ROM), flash memory, or other electrical or electrostatic storage medium; or so forth.

As illustrated in FIG. 1, the digital processor 30 is configured to detect and validate an ECG alarm. A detected ECG signal 40 is processed by an asystole detector 42 to detect a "flatline" condition in which the ECG signal does not exhibit pulsatile behavior indicative of a beating heart. At a decision block 44 it is determined whether asystole has been detected based on the ECG signal 40 alone. Regardless of whether asystole is detected, the processing blocks 40, 42, 44 cycle repetitively in order to provide continuous ECG signal monitoring for an asystole condition. This is indicated by the loopback arrow in FIG. 1 labeled with the decision "Yes or No".

If at the decision block 44 it is determined that an asystole event has been detected based on the ECG signal 40 alone (indicated by the arrow in FIG. 1 labeled with the decision "Yes"), the asystole alarm condition is validated based on a pleth signal 50 that is monitored by the plethysmogram implemented by the patient monitor 20 and sensor 16. The illustrative pleth signal 50 may be replaced by an APB signal or other secondary physiological signal that exhibits a pulsatile signal component with substantial regularity in pulse interval and pulse amplitude during the normal physiological condition. To validate the asystole alarm generated by the ECG alone, the pleth signal 50 (or other secondary physiological signal with a pulsatile component that is not an ECG signal) is processed by a pulse regularity index (PRI) computation block 52 to generate a pulse regularity index (PRI) quantifying pulse regularity of the pulsatile component of the monitored second physiological signal 50. The computed PRI is compared in a comparison block 54 with a validation criterion. Based on this comparison, an asystole alarm validation block 56 decides whether the asystole alarm generated by the ECG alone should be validated. If the asystole alarm is validated, then a human-perceptible asystole alarm 58 is issued, for example by activating the audio speaker 26 to emit an audibly perceptible asystole alarm, and/or by showing the visually perceptible alarm indicator 24 on the display 22 of the patient monitor 20, or by activating an audible and/or visual alarm at a nurses' station (not shown), or so forth.

The validation criterion is suitably determined by training the detecting and validating operations respective to a training set of ECG signals and second physiological signals concurrently acquired from a plurality of calibration patients, in which the training set has asystole conditions labeled. For example, based on this training a threshold value is suitably determined for the PRI such that every actual asystole event is properly validated (no false negatives) and a substantial number of asystole alarm events generated by the ECG alone are invalidated by comparison of the PRI with the trained threshold value. In some embodiments, the training may be performed for patients of different characteristics in order to generate different validation criteria for different classes of patients. For example, the illustrated embodiment of FIG. 1 was trained for different age classes (e.g., infant age class, pediatric age class, adult age class, elderly age class) and a PRI definition and validation criterion selector 60 selects the PRI definitions for use in the compute PRI block 52 and the validation criterion for use in the comparison block 54 based on an inputted patient age 62. Adjustment for different patient classes can take the form of adjustment of the threshold criterion, or adjustment of the definition of the quantitative PRI formula or definition, or both.

Figure 2:
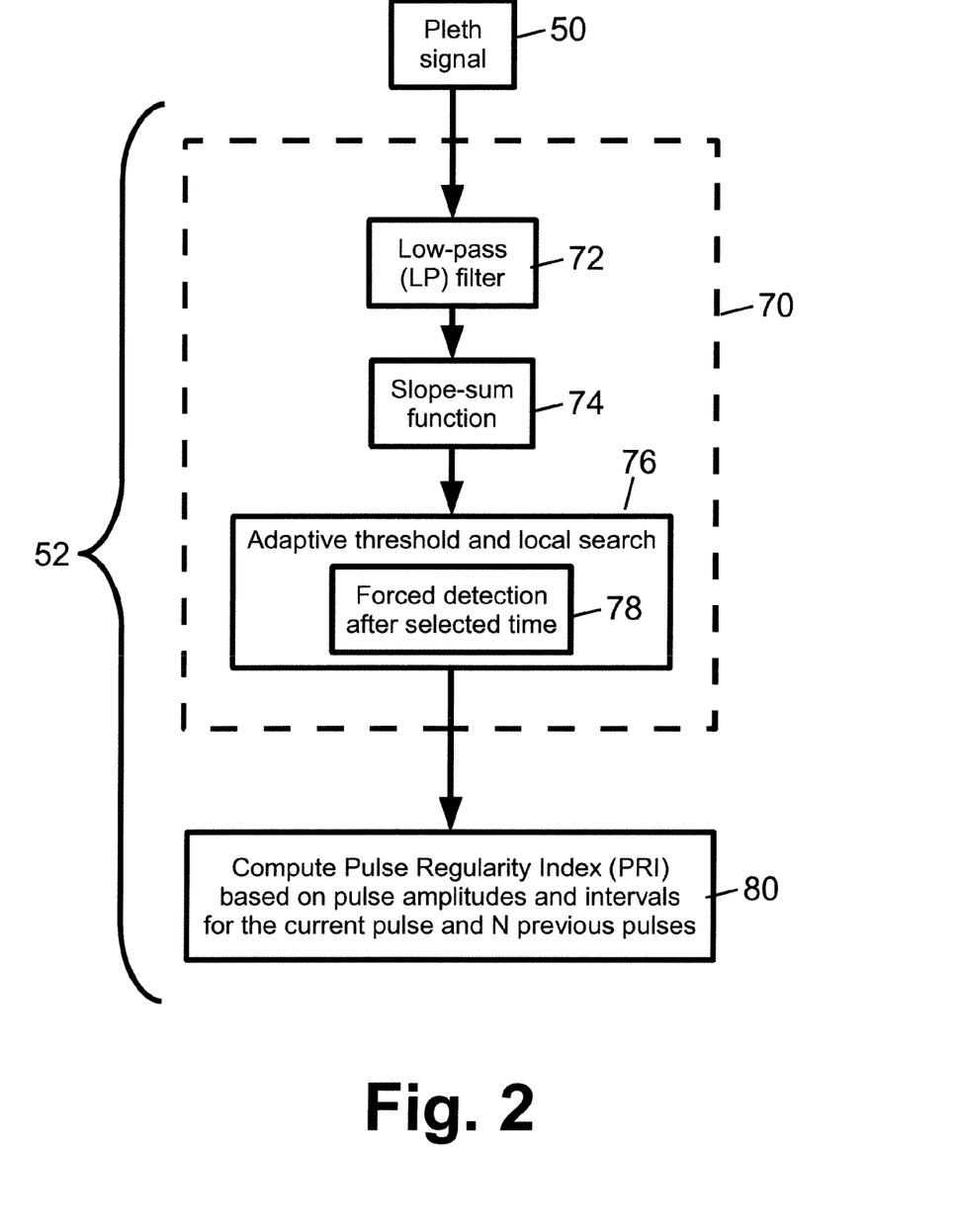
FIG. 2 diagrammatically shows the pulse regularity index (PRI) computation component of FIG. 1 in additional detail.

With reference to FIG. 2, an illustrative implementation of the pulse regularity index (PRI) computation block 52 is described as an illustrative example. In general, the PRI computation entails a pulse detector 70 which detects pulses of the pulsatile component of the secondary physiological signal, and a PRI computation 80 based on pulse amplitude and pulse interval information for the detected pulses. In the illustrated embodiment of FIG. 2, the PRI is calculated on a pulse-by-pulse basis for a current pulse based on the current pulse and N immediately preceding pulses. The value of the positive integer N is selected to provide sufficient information for a meaningful estimate of the pulse amplitude and pulse interval regularity at the time of the current pulse, but should be short enough to provide a PRI that is not unduly influenced by substantially earlier pulsatile behaviour. In general, N should be greater than or equal to two, and in some embodiments is greater than or equal to three. In some illustrative examples, N=4 is used, so that the N+1 pulses analyzed (including the current pulse and the N immediately preceding pulses) constitute five pulses in total. Assuming the pulsatile signal is consonant with a heart rate of around 60-150 beats per minute, N+1=5 pulses amounts to between about two seconds and five seconds worth of information. Again, other values for N may be used. For each current pulse, a PRI is computed based on the rhythm and amplitude features derived from the current pulse and the immediately preceding N pulses. To validate an ECG asystole alarm, only the PRI from the current pulse just before, at, or just after the asystole alarm event is checked in order to validate the asystole alarm event.

In general, the pulse detection 70 can consider either peak or onset of the pulse as the fiducial point for the pulse time. In illustrative FIG. 2, the pulse detection 70 is performed using a method similar to that described in Zong et al., "An open-source algorithm for detection of ABP pulse onset", Computers in Cardiology, 29:345-48 (2003), which is incorporated herein by reference in its entirety. This method uses pulse onset as the fiducial point. The monitored pleth signal 50 is filtered by a low-pass filter 72, for example having a cutoff frequency of about 15 Hz (although other cutoff frequencies are contemplated). The low-pass filtered pleth signal is then converted to a slope-sum function (SSF) signal by a slope-sum function 74, which facilitates the pulse onset detection. An adaptive threshold and local search 76 is applied to SSF signal to find the pulse and a local search process locates the onset of the pulse.

A problem can arise, however, if the secondary physiological signal 50 does not have a pulsatile component. This might indeed be expected, for example, during an actual asystole event. To address this situation, a forced pulse detection 78 is provided, which defines one or more pulses of the set of N+1 pulses as a forced pulse detection conditional upon the pulsatile component of the monitored second physiological signal 50 having no pulses in a preselected time interval. That is, when no pulse is detected for more than 2 seconds (or for another preselected time interval) since the last detected pulse, a forced pulse detection is defined as one of the N+1 pulses. The forced pulse detection is labelled as such so that it is specially treated during the PRI computation 80. Alternatively, it is contemplated to assign a forced pulse detection a default amplitude and default pulse interval (respective to its nearest-neighbor pulses).

The PRI generation operation 80 takes the time series of N+1 pulses as input. In this illustrative PRI computation example, any forced pulse detection generated by the operation 78 is treated as same as the normal pulse detection for the later on pulse interval and amplitude feature analysis. For each pulse (including, in this example, any forced pulse detection), pulse amplitude and interval information is computed as statistical pulse-to-pulse (PP) interval features and statistical pulse amplitude features analyzed over the N+1 pulses. The PP interval and amplitude statistics can be done in the following way: For the current pulse denoted $P_i$ and the N immediately preceding pulses denoted $P_{i-n}$, n=1, ..., N, calculate the following variables: (i) number of the forced-detections denoted $FD_{NUM}$; (ii) mean value of the pulse-to-pulse interval (PPI) denoted $PPI_{MEAN}$; (iii) standard deviation of the PPI denoted $PPI_{SD}$; (iv) mean value of the N+1 pulse amplitudes denoted $PPA_{MEAN}$; and (iv) standard deviation of the N+1 pulse amplitudes denoted $PPA_{SD}$.

In this illustrative PRI computation example, fuzzy variables are used to represent the statistical features of the pulse amplitude and interval information. The following three fuzzy variables are defined: '$PPI_{MEAN}$_is_Reasonable', and '$PPI_{SD}$_is_Small', and '$PPA_{SD}$_is_Small'. Standard functions, namely the S-function and the Z-function, are used as the membership functions. The S-function and Z-function are defined as follows:

$$S(x; a, b) = \begin{cases} 0, & x \leq a \\ 2 \cdot \left(\frac{x-a}{b-a}\right)^2, & a < x \leq \frac{a+b}{2} \\ 1 - 2 \cdot \left(\frac{x-b}{b-a}\right)^2, & \frac{a+b}{2} < x \leq b \\ 1, & b < x, \end{cases} \quad (1)$$

and $$Z(x; a, b) = 1 - S(x; a, b). \quad (2)$$

Using the S-function and Z-function as membership functions, the fuzzy variables are defined as follows for this illustrative PRI computation example:

'PPI$_{MEAN}$_is_Reasonable' (PPI-Mean-R)

$$\mu_{PPI\text{-}Mean\text{-}R} = S(PPI_{MEAN};200,400) \wedge Z(PPI_{MEAN};1500,2000) \quad (3),$$

where PPI$_{MEAN}$ is the mean value of the PPI among the considered N+1 pulse detections; the unit of the parameters is ms; and operator $\wedge$ is the standard fuzzy intersection: $\mu_A \wedge \mu_B = \min[\mu_A, \mu_B]$. 'PPI$_{SD}$_is_Small' can be defined using Z-function as the membership function:

'PPI$_{SD}$_is_Small' (PPI-SD-S)

$$\mu_{PPI\text{-}SD\text{-}S} = Z(PPI_{SD}/PPI_{MEAN};0.1,0.2) \quad (4)$$

where PPI$_{SD}$ is the standard deviation of the PPI among the considered N+1 pulse detections. "PPA$_{SD}$_is_Small" can be defined using the Z-function as the membership function:

'PPA$_{SD}$_is_Small' (PPA-SD-S)

$$\mu_{PPA\text{-}SD\text{-}S} = Z(PPA_{SD}/PPA_{MEAN};0.1,0.2) \quad (5)$$

where PPA$_{SD}$ is the standard deviation of the pulse-by-pulse amplitude (PPA) and PPI$_{MEAN}$ is the mean value of the PPA, among the considered N+1 pulse detections. In addition, a binary variable, "No_Forced_Detections" is defined using the Boolean function:

'No_Forced_Detections' (NFD)

$$\mu_{NFD} = \text{Boolean}(\text{'FD}_{Count}==0\text{'}) \quad (6),$$

where, FD$_{Count}$ is the number of the forced-detections among the considered N+1 pulse detections; Boolean(True)=1, Boolean(False)=0. A composite fuzzy variable, 'Pulses_are_Regular', is derived from the following fuzzy logic reasoning (i.e., fuzzy conditional statement):

| | |
|---|---|
| IF | 'No_Forced_Detections' AND |
| | 'PPI$_{MEAN}$_is_Reasonable' AND |
| | ('PPI$_{SD}$_is_Small' OR 'PPA$_{SD}$_is_Small') |
| THEN | 'Pulses_are_Regular' |
| | $\mu_{Pulses\_are\_Regular} =$ |
| | $\mu_{NFD} \wedge \mu_{PPI\text{-}mean\text{-}R} \wedge (\mu_{PPI\text{-}SD\text{-}S} \wedge \mu_{PPA\text{-}SD\text{-}S})$ |

(7)

where $\mu_{NFD}$, $\mu_{PPI\text{-}mean\text{-}R}$, $\mu_{PPI\text{-}SD\text{-}S}$, and $\mu_{PPA\text{-}SD\text{-}S}$ are from Equations (3)-(6), and the operator $\wedge$ is the standard fuzzy union: $\mu_A \wedge \mu_B = \max[\mu_A, \mu_B]$. The fuzzy variable 'Pulses_are_ Regular' has a value between 0 and 1 with the value 1 representing the best short-term pulse regularity and the value 0 representing the worst short-term pulse regularity (that is, substantially no pulse regularity). The PRI value is assigned to the value of fuzzy variable 'Pulses_are_Regular':

$$PRI = \mu_{Pulses\_are\_Regular} \quad (8).$$

The illustrative PRI computation works in the following way: For a secondary physiological signal (e.g., the illustrative pleth signal 50, or an APB signal), the onset (or, alternatively, the peak or other fiducial) of each pulse is detected. If there is no pulse detectable for more than 2 seconds (or another preselected time interval), then a forced pulse detection is applied. For each detected pulse (or forced pulse detection), a value of the PRI is computed according to Equation (8) and is associated with the pulse. The PRI indicates short-term pulse regularity associated to the pulse, where "short term" is defined by the time interval of the N+1 pulses including the current pulse which are taken into consideration in computing the PRI.

The above PRI definition is for the class of adult patients. For patients of other classes (for example, pediatric patients) the PRI definition selector and validation criterion selector may adjust the PRI value, or the threshold criterion, or both in order to provide useful validation operation for these patients.

Figure 3:
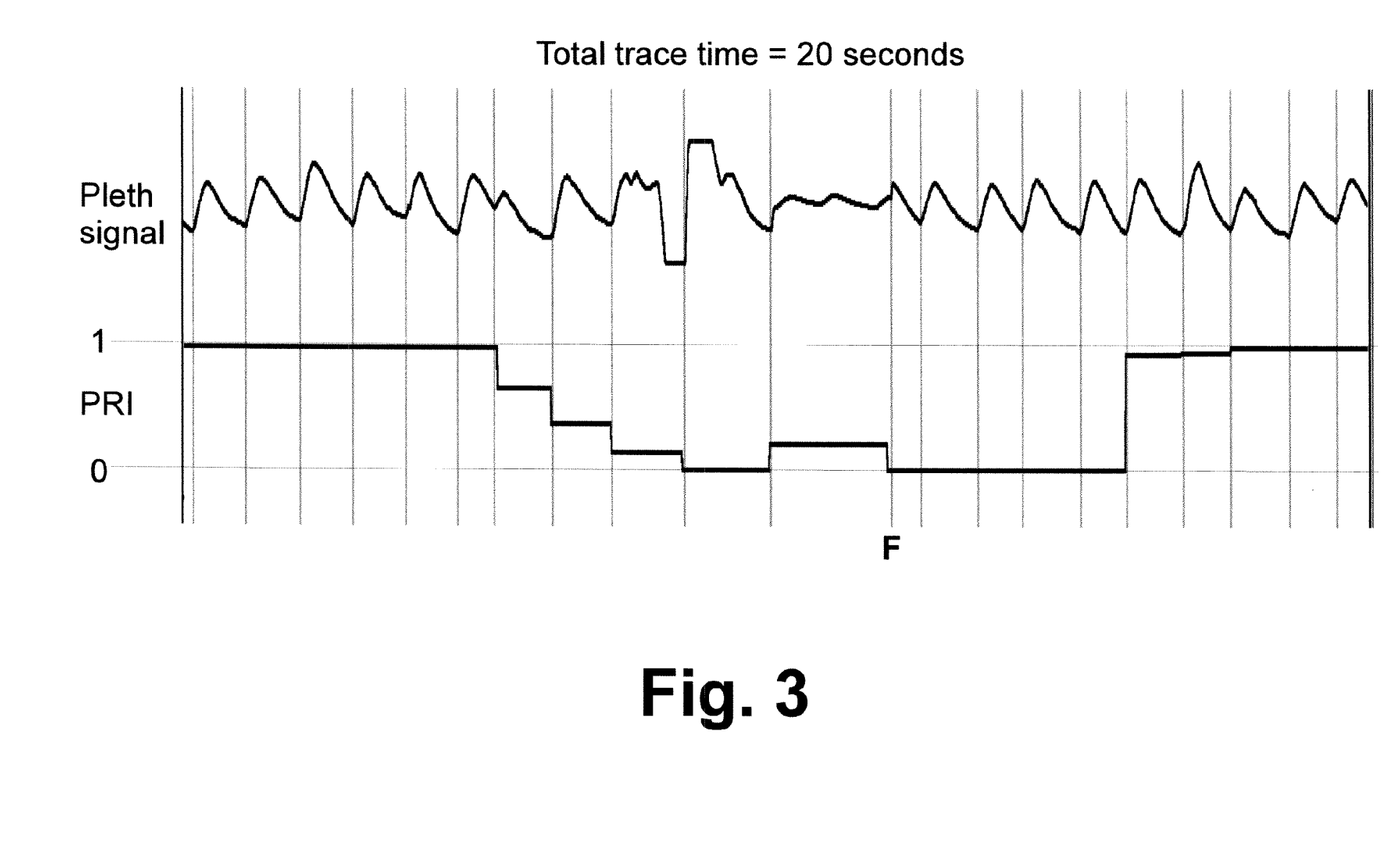
FIG. 3 diagrammatically shows a plethysmogram (pleth) signal along with a pulse regularity index (PRI) computed from the pleth signal.

With reference to FIG. 3, an example of the illustrative PRI computation is displayed. The top trace of FIG. 3 shows the source pleth signal, while the bottom trace of FIG. 3 shows the PRI computed using Equation (8), with N=4. Each vertical line in FIG. 3 denotes a pulse onset. A single forced pulse detection was employed, as denoted by the label "F" on the vertical line corresponding to the forced pulse detection. As expected, the PRI has a value of unity (1) in regions where the pleth signal has a visually manifest regularity, and the PRI decreases to a value of zero (0) in the central region of FIG. 3 where the regularity of the pleth signal has visually manifest irregularity.

With reference back to FIG. 1, in comparison block 54 the PRI is compared with the validation criterion to validate the asystole alarm generated by the ECG. At a time i when an ECG asystole alarm is issued, the PRI associated with the last pulse prior to or synchronous with time i is compared with the validation criterion. For the illustrative PRI computation example, the validation criterion is suitably a validation threshold denoted Thr—if the PRI is greater than the validation threshold Thr (that is, PRI>Thr), then the asystole alarm generated by the ECG alone is rejected as a false alarm; otherwise, the asystole alarm is accepted as a true alarm at decision block 56, and the human-perceptible asystole alarm 58 is activated.

In the illustrated embodiments, there is only one secondary physiological signal (the illustrated pleth signal 50) for use in the validation. If two (or more) secondary physiological signals are available for the validation, they can be used by computing a PRI for each secondary physiological signal and choosing one of the computed PRI. For the example case in which a larger PRI indicates more pulse regularity, the validation criterion is suitably a threshold which must be exceeded in order to override the ECG asystole alarm. In this case, the maximum PRI computed from the two available secondary physiological signals (for example, both pleth and ABP signals available) is suitably used in the comparison block 54.

The window size N and the validation threshold Thr can be optimized using set of training data with annotated ECG asystole alarms and their associated ECG and secondary physiological (e.g., ABP or Pleth) signals. In an actually conducted training session, N=4 and Thr=0.5 were selected by the training. For the training, an annotated dataset of 65 records was used, of which all records have pleth signal data and 11 records also have ABP signal data). This training set was selected from 756 intensive care unit patients, and provides a total of 1916 hours (with an average of 28 hours/record) of continuous ECG signal and concurrent ABP and/or Pleth signals. The training set included 147 asystole alarms as indicated by ECG alone. Of these 147 alarms, 15 alarms were true positives (that is, actual asystole events) and 132 were false positives as judged by human expert. The trained validation system using only the pleth signal for validation rejected 46% of the false ECG asystole alarms without rejecting any of the 15 true asystole alarm events. When the ABP signal (when available) was used to replace the pleth signal in the validation system, 52% of false ECG asystole alarms were overridden, again without rejecting any true asystole alarm event. When using both ABP (when available) and pleth, 59% of false ECG alarms were rejected, again without rejecting any true asystole alarm event.

Figure 4:
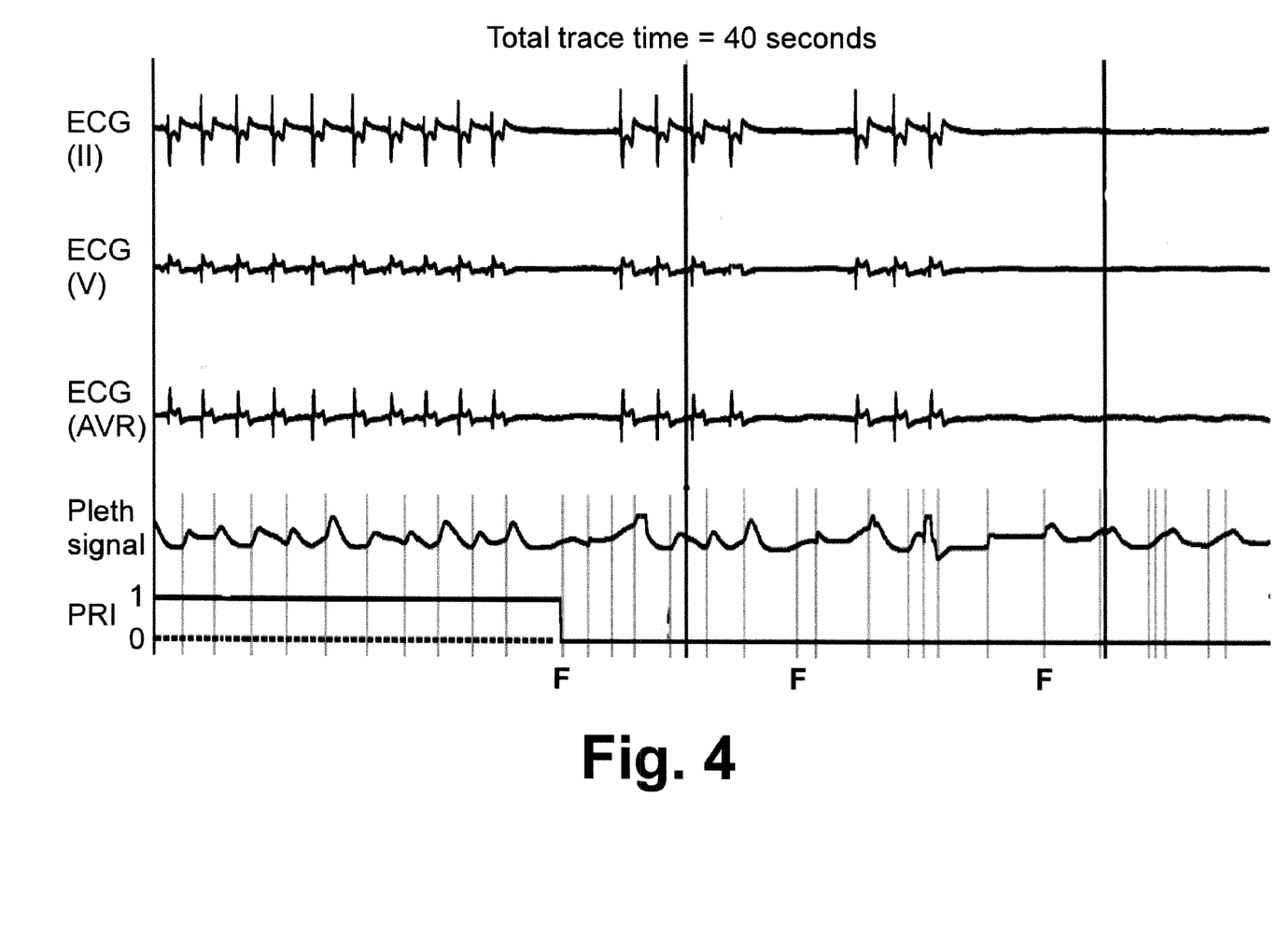
FIG. 4 diagrammatically shows a three-channel ECG signal, a concurrently monitored plethysmogram (pleth) signal, and a pulse regularity index (PRI) computed from the pleth signal, for a time interval including two true asystole events.

With reference to FIG. 4, an example is shown where a true ECG asystole alarm was properly kept (that is, validated as true alarm) by the validation system of FIG. 1 trained as described herein. The topmost three traces show a three-channel ECG. Two (true) asystole alarms were issued by the ECG-based asystole detector, as indicated by the thick vertical lines that pass through the three-channel ECG traces. The second-from bottom trace is the concurrently acquired pleth signal, while the bottommost trace is the PRI computed from the pleth signal. When ECG asystole happened, the pleth signal lost regularity and the computed PRI decreased to zero, even though there were still pulsations due to respiration in the pleth signal. At the time of each of the two (true) ECG asystole alarms, it is observed that the PRI value is low (essentially zero) and lower than Thr=0.5 which was the trained threshold, both ECG asystole alarms are validated as true positive asystole alarms. In the bottom two plots, lighter vertical lines that pass through only the lowermost two curves (that is, the pleth and PRI curves) indicate the pulse onset detections. Three forced pulse detections are indicated by vertical lines labelled by "F".

Figure 5:
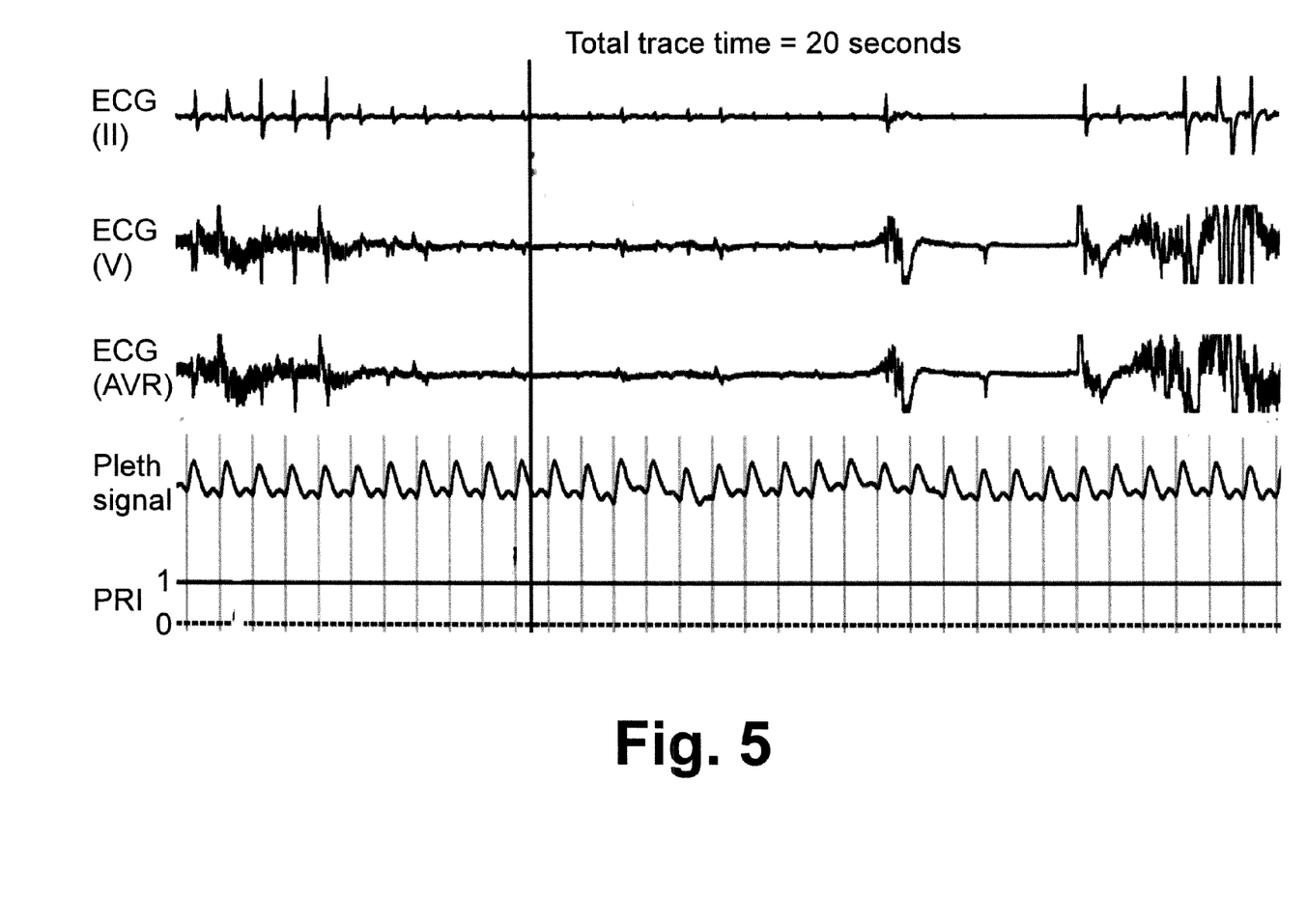
FIG. 5 diagrammatically shows a three-channel ECG signal, a concurrently monitored plethysmogram (pleth) signal, and a pulse regularity index (PRI) computed from the pleth signal, for a time interval including one false asystole event.

With reference to FIG. 5, an example of a false ECG asystole alarm is shown, which was rejected (that is, not validated) by the validation system of FIG. 1 trained as described herein. The topmost three traces show a three-channel ECG. A single (false) asystole alarm was issued by the ECG-based asystole detector, as indicated by the thick vertical line passing through the three-channel ECG traces. The second-from bottom trace is the concurrently acquired pleth signal, while the bottommost trace is the PRI computed from the pleth signal. The false ECG asystole event was issued due to the reduced amplitude of the ECG signals. However, the pleth signal continued to behave regularly during this ECG asystole event, and the computed PRI remained at 1 indicating a high degree of pulsatile regularity. At the onset of the (false) ECG asystole event, the PRI was larger than the trained Thr=0.5, and so the ECG asystole alarm was rejected (that is, was not validated).

In the foregoing illustrative embodiments, the alarm condition is an asystole alarm condition that is detected using the ECG and validated based on quantification of pulse regularity of the secondary physiological signal (e.g., pleth and/or APB signal). However, other alarm conditions can be detected and validated using the disclosed techniques. For example, a ventricular fibrillation alarm event is readily detected from the ECG signal. Validation of a detected ventricular fibrillation event similarly can be validated based on quantification of pulse regularity of the secondary physiological signal (e.g., pleth and/or APB signal) as disclosed herein. For validation of a ventricular fibrillation alarm event, it is contemplated that it may be advantageous to employ additional noise rejection filtering, since a ventricular fibrillation alarm event does not entail complete stoppage of heart pulsations but rather randomization of heart pulsations. The training of the validation criterion for validating ventricular fibrillation alarm events should employ training data with ventricular fibrillation alarm events labeled, either alone or in addition to labeling of asystole events (if present in the training data).

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. A patient monitor comprising:
   an electrocardiograph monitoring an electrocardiographic signal of a patient;
   a secondary physiological signal monitor monitoring a second physiological signal of the patient concurrently with the electrocardiograph monitoring the electrocardiographic signal of the patient;
   an alarm condition detector configured to detect an asystole alarm condition in which the electrocardiographic signal of the patient does not exhibit pulsatile behavior indicative of a beating heart;
   an alarm condition validator configured to validate the asystole alarm condition based on whether a pulse regularity index (PRI) quantifying pulse regularity of a pulsatile component of the concurrently monitored second physiological signal of the patient satisfies a validation criterion, the PRI being computed based on a set of N+1 pulses including (i) a current pulse of the pulsatile component of the monitored second physiological signal and (ii) N immediately preceding pulses of the pulsatile component of the monitored second physiological signal, where N is a positive integer greater than or equal to two, wherein the alarm condition validator is configured to define one or more pulses of the set of N+1 pulses as a forced pulse detection conditional upon the pulsatile component of the monitored second physiological signal having no pulses in a preselected time interval and wherein the PRI is computed based on (i) amplitude information for the pulses of the set of N+1 pulses including any forced pulse detections, (ii) time interval information between the pulses of the set of N+1 pulses including any forced pulse detections, and (iii) the number of forced pulse detections; and
   an alarm indicator configured to generate a human perceptible alarm conditional upon both the alarm condition detector detecting an asystole alarm condition and the asystole alarm condition validator validating the asystole alarm condition.

2. The patient monitor as set forth in claim 1, wherein the secondary physiological signal monitor is selected from a group consisting of:
   an arterial blood pressure (ABP) monitor monitoring arterial blood pressure of the patient concurrently with the electrocardiograph monitoring the electrocardiographic signal of the patient, and
   a plethysmogram monitoring a plethysmogram signal of the patient concurrently with the electrocardiograph monitoring the electrocardiographic signal of the patient.

3. A The patient monitor as set forth in claim 1 wherein the alarm condition validator is configured to select at least one of:
   (i) a definition of the PRI and
   (ii) the validation criterion
based on patient age.

4. The patient monitor as set forth in claim 1, wherein:
   the secondary physiological signal monitor monitors at least two different second physiological signals of the patient concurrently with the electrocardiograph monitoring the electrocardiographic signal of the patient; and the asystole alarm condition validator is configured to compute the PRI for each of the at least two different second physiological signals and to validate the asystole alarm condition based whether the largest computed PRI satisfies the validation criterion.

5. The patient monitor as set forth in claim 1, wherein the asystole alarm condition validator is configured to extract the pulsatile component of the monitored second physiological signal from the monitored second physiological signal using signal processing including at least low pass filtering.

6. The patient monitor as set forth in claim 1, wherein N is a positive integer equal to 2, 3, or 4.

7. A patient monitoring method comprising:
monitoring an electrocardiographic signal of a patient;
monitoring a second physiological signal of the patient concurrently with the monitoring of the electrocardiographic signal of the patient;
detecting an asystole alarm condition in which the electrocardiographic signal of the patient is Ratline;
validating the asystole alarm condition based on short-term pulse regularity of a pulsatile component of the concurrently monitored second physiological signal of the patient, the validating including:
    detecting N+1 pulses including a current pulse and N immediately preceding pulses of the pulsatile component of the concurrently monitored second physiological signal of the patient where N is a positive integer greater than or equal to two;
    computing a pulse regularity index (PRI) quantifying pulse regularity of the N+1 detected pulses based on (i) mean value of the N+1 pulse amplitudes of the N+1 pulses, (ii) standard deviation of the N+1 pulse amplitudes of the N+1 pulses, (iii) mean value of the pulse-to-pulse interval (PPI) between successive pulses of the N+1 pulses, and (iv) standard deviation of the PPI; and
    comparing the PRI with a validation criterion; and
generating a human perceptible alarm conditional upon the alarm condition being validated by the validating.

8. The patient monitoring method as set forth in claim 7, further comprising:
determining the validation criterion based on training the detecting and validating operations respective to a training set of electrocardiographic signals and second physiological signals concurrently acquired from a plurality of calibration patients wherein the training set has asystole conditions labeled.

9. The patient monitoring method as set forth in claim 7, wherein:
the detecting N+1 pulses comprises detecting at least one of the N+1 pulses as a forced pulse detection conditional upon a failure to detect a pulse; and
the PRI is computed further based on (v) the number of forced pulse detections included in the N+1 pulses.

10. The patient monitoring method as set forth in claim 7, wherein N is a positive integer greater than or equal to three.

11. The patient monitoring method as set forth in claim 7, wherein N is a positive integer equal to 2, 3, or 4.

12. A non-transitory storage medium storing instructions executable by a digital processor to perform a patient monitoring method comprising:
monitoring an electrocardiographic signal of a patient;
monitoring a second physiological signal of the patient concurrently with the monitoring of the electrocardiographic signal of the patient;
detecting an asystole alarm condition in which the electrocardiographic signal of the patient is Ratline;
validating the asystole alarm condition based on short-term pulse regularity of a pulsatile component of the concurrently monitored second physiological signal of the patient, the validating including:
    detecting N+1 pulses including a current pulse and N immediately preceding pulses of the pulsatile component of the concurrently monitored second physiological signal of the patient where N is a positive integer greater than or equal to two;
    computing a pulse regularity index (PRI) quantifying pulse regularity of the N+1 detected pulses based on (i) mean value of the N+1 pulse amplitudes of the N+1 pulses, (ii) standard deviation of the N+1 pulse amplitudes of the N+1 pulses, (iii) mean value of the pulse-to-pulse interval (PPI) between successive pulses of the N+1 pulses, and (iv) standard deviation of the PPI; and
    comparing the PRI with a validation criterion; and
generating a human perceptible alarm conditional upon the alarm condition being validated by the validating.

\* \* \* \* \*

UNITED STATES PATENT AND TRADEMARK OFFICE
CERTIFICATE OF CORRECTION

PATENT NO. : 8,989,853 B2
APPLICATION NO. : 13/321841
DATED : March 24, 2015
INVENTOR(S) : Wei Zong It is certified that error appears in the above-identified patent and that said Letters Patent is hereby corrected as shown below:

In the Claims

Claim 7, Lines 6-7 currently says:
"detecting an asystole alarm condition in which the electro cardiographic signal of the patient is Ratline"
And should read:
"detecting an asystole alarm condition in which the electro cardiographic signal of the patient is flatline"

Claim 12, Lines 8-9 currently says:
"detecting an asystole alarm condition in which the electro cardiographic signal of the patient is Ratline"
And should read:
"detecting an asystole alarm condition in which the electro cardiographic signal of the patient is flatline"

Signed and Sealed this
Sixth Day of June, 2023

Katherine Kelly Vidal
*Director of the United States Patent and Trademark Office*